(12) United States Patent
Ito et al.

(10) Patent No.: US 11,122,966 B2
(45) Date of Patent: Sep. 21, 2021

(54) ENDOSCOPE AND EXTERIOR COVER FOR ENDOSCOPE

(71) Applicant: OLYMPUS CORPORATION, Tokyo (JP)

(72) Inventors: Takayasu Ito, Hino (JP); Eiji Matsuda, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 351 days.

(21) Appl. No.: 16/042,237

(22) Filed: Jul. 23, 2018

(65) Prior Publication Data

US 2018/0325355 A1     Nov. 15, 2018

Related U.S. Application Data

(63) Continuation of application No. PCT/JP2016/078085, filed on Sep. 23, 2016.

(30) Foreign Application Priority Data

Jan. 25, 2016    (JP) .............................. JP2016-011466

(51) Int. Cl.
    *A61B 1/005*       (2006.01)
    *G02B 23/24*       (2006.01)
    (Continued)

(52) U.S. Cl.
    CPC ........ *A61B 1/0052* (2013.01); *A61B 1/00066* (2013.01); *A61B 1/00137* (2013.01); (Continued)

(58) Field of Classification Search
    CPC .............. A61B 1/0052; A61B 1/00142; A61B 1/00066; A61B 1/00039; A61F 2009/2407; A61F 2300/1068; A61F 13/98
    (Continued)

(56) References Cited

U.S. PATENT DOCUMENTS

| | | | | |
|---|---|---|---|---|
| 2002/0050181 A1* | 5/2002 | Kaji | ......................... | F16J 3/043 74/18 |
| 2004/0193014 A1* | 9/2004 | Miyagi | .............. | A61B 1/00039 600/146 |

(Continued)

FOREIGN PATENT DOCUMENTS

| | | |
|---|---|---|
| JP | S52-160043 U1 | 12/1977 |
| JP | S54-024818 U1 | 2/1979 |

(Continued)

OTHER PUBLICATIONS

International Search Report dated Dec. 20, 2016 issued in PCT/JP2016/078085.

*Primary Examiner* — Matthew J Kasztejna
(74) *Attorney, Agent, or Firm* — Scully, Scott, Murphy & Presser, P.C.

(57) ABSTRACT

An endoscope according to one aspect of the present invention includes: an operation lever portion that is provided in an operation portion, includes an operation shaft, and is capable of adjusting a bending angle of a bending portion in conjunction with a tilting operation; and an exterior cover that is water-tightly fixed to the operation portion so as to cover an outer periphery of the operation shaft, and is formed in a stair shape in cross section, including a hardly deformed region and an easily deformed region that is formed at a predetermined angle with respect to the hardly deformed region.

19 Claims, 4 Drawing Sheets

(51) Int. Cl.
*A61B 1/00* (2006.01)
*A61B 1/01* (2006.01)
A61B 1/05 (2006.01)
A61B 1/07 (2006.01)

(52) U.S. Cl.
CPC ............ *A61B 1/00142* (2013.01); *A61B 1/01* (2013.01); *G02B 23/24* (2013.01); *G02B 23/2476* (2013.01); A61B 1/05 (2013.01); A61B 1/07 (2013.01)

(58) Field of Classification Search
USPC .................................................. 600/146–147
See application file for complete search history.

(56) References Cited

U.S. PATENT DOCUMENTS

| | | | | |
|---|---|---|---|---|
| 2004/0267093 | A1* | 12/2004 | Miyagi | A61B 1/00039 600/146 |
| 2009/0149709 | A1* | 6/2009 | Koitabashi | A61B 1/00149 600/131 |
| 2016/0192823 | A1 | 7/2016 | Yasunaga et al. | |
| 2017/0196435 | A1* | 7/2017 | Sato | G02B 23/2476 |
| 2018/0317748 | A1* | 11/2018 | Hatano | A61B 1/00066 |
| 2019/0133419 | A1* | 5/2019 | Hatano | A61B 1/0057 |
| 2019/0254503 | A1* | 8/2019 | Hatano | A61B 1/00 |

FOREIGN PATENT DOCUMENTS

| | | | | |
|---|---|---|---|---|
| JP | 2004-321612 | A | 11/2004 | |
| JP | 5861017 | B1 | 2/2016 | |
| JP | 2016052422 | * | 4/2016 | ............... A61B 1/00 |

* cited by examiner

ENDOSCOPE AND EXTERIOR COVER FOR ENDOSCOPE

CROSS REFERENCE TO RELATED APPLICATION

This application is a continuation application of PCT/JP2016/078085 filed on Sep. 23, 2016 and claims benefit of Japanese Application No. 2016-011466 filed in Japan on Jan. 25, 2016, the entire contents of which are incorporated herein by this reference.

BACKGROUND OF THE INVENTION

1. Field of the Invention

The present invention relates to an endoscope, in which a bending portion is caused to perform a bending action in conjunction with an operation to tilt toward an operation lever, and relates to an exterior cover for the endoscope.

2. Description of the Related Art

In order to observe a location inside a subject such as inside a living body or a structure where observation is difficult to perform, an endoscope that is insertable into a subject has been in wide use in the medical field or the industrial field, for example.

An insertion portion of such an endoscope is provided with a bending portion aimed to improve insertability and observability inside a subject. This bending portion is caused to perform a bending operation by a bending operation device provided in an operation portion.

As for the bending operation device, for example as disclosed in Japanese Patent Application Laid-Open Publication No. 2004-321612, a joystick type is widely known, a bending portion of which is caused to perform a bending operation by an operation to tilt toward an operation lever.

In such a conventional bending operation device of the joystick type, the outside of the operation lever is water-tightly covered with an exterior cover made of an elastic member such as rubber in order to ensure water-tightness inside an endoscope while allowing a tilting operation of a bending lever protruding outside the operation portion.

Endoscopes of the above type are subject to a leak test, prior to after-use cleaning, to determine whether or not the internal water-tightness has been ensured. The leak test is generally conducted by application of positive pressure to the inside of the endoscope, manually by a user or automatically by an endoscope cleaner, through a ventilation portion provided in the endoscope.

SUMMARY OF THE INVENTION

An endoscope according to one aspect of the present invention is provided with: an operation portion that is provided on a proximal end side of an insertion portion including a bending portion; an operation lever portion that is provided in the operation portion, includes an operation shaft, and is capable of adjusting a bending angle of the bending portion in conjunction with a tilting operation; and an exterior cover that is water-tightly fixed to the operation portion so as to cover an outer periphery of the operation shaft, and is formed in a stair shape including a first deformation portion and a second deformation portion that is formed at a predetermined angle with respect to the first deformation portion and deformed more easily than the first deformation portion.

An exterior cover for an endoscope according to one aspect of the present invention is provided in an operation portion of the endoscope, and water-tightly fixed to the operation portion so as to cover an outer periphery of an operation shaft capable of performing a tilting operation. In the exterior cover, a first deformation portion and a second deformation portion are formed in a stair shape, the second deformation portion having a predetermined angle with respect to the first deformation portion and being deformed more easily than the first deformation portion.

An endoscope according to another aspect of the present invention is an endoscope provided with an exterior cover, which is provided in an operation portion of the endoscope, and water-tightly fixed to the operation portion so as to cover an outer periphery of an operation shaft capable of performing a tilting operation, and in which a first deformation portion and a second deformation portion are formed in a stair shape, the second deformation portion having a predetermined angle with respect to the first deformation portion and being deformed more easily than the first deformation portion.

DETAILED DESCRIPTION OF THE PREFERRED EMBODIMENT

Figure 1:
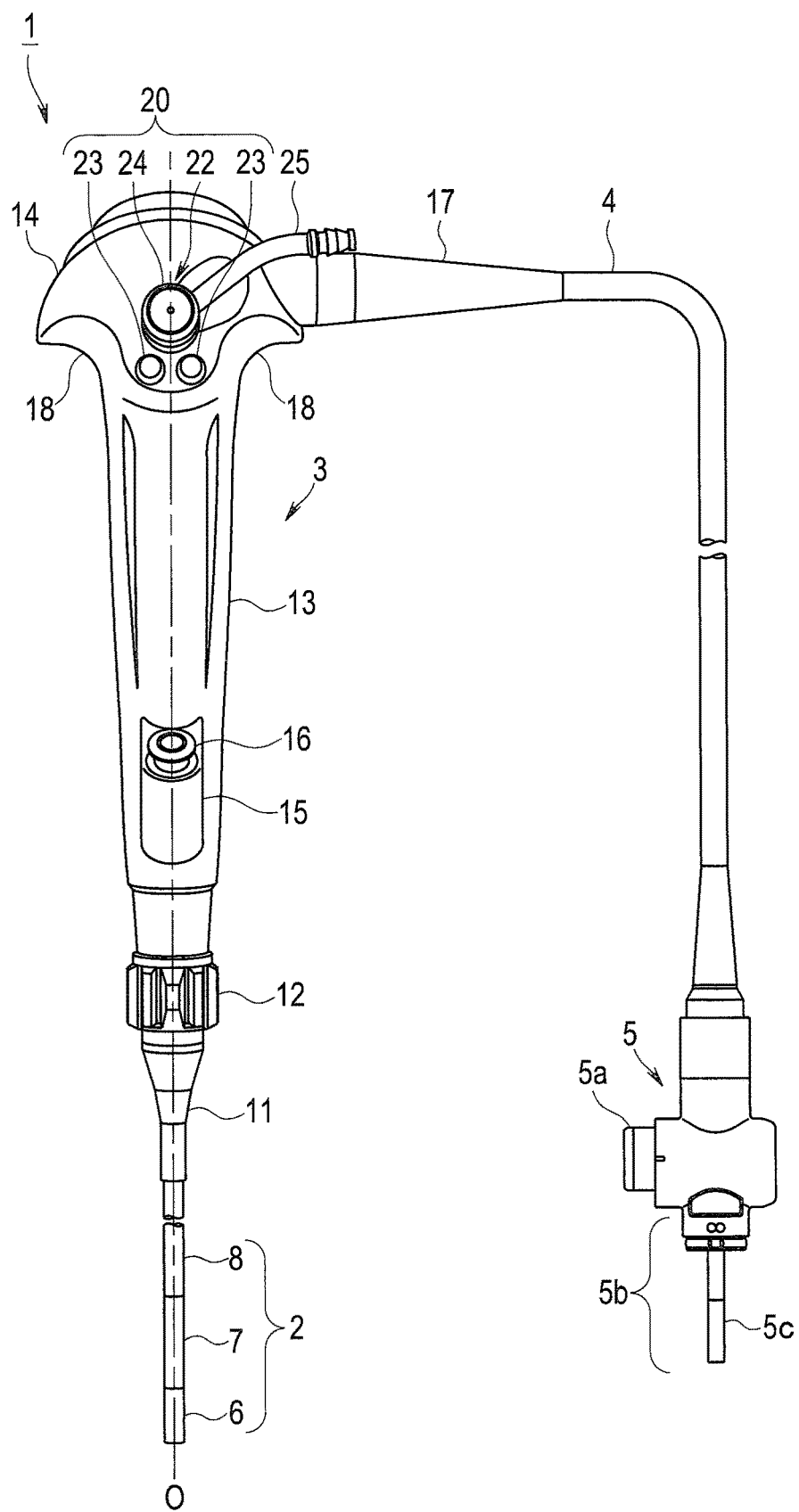
FIG. 1 is a front view showing an appearance configuration of an endoscope according to one aspect of the present invention.

A preferred embodiment of the present invention will be described below with reference to the drawings. In each of the drawings to be used in the following description, each component is made different in scale so as to have a size recognizable on the drawing, and the present invention is not restricted only to quantities of the components, shapes of the components, size ratios of the components, and relative positional relationship among the components, which are described in the drawings. Further, in the following description, vertically upper and lower portions on the drawings may be described as upper and lower portions of the component.

First, an endoscope according to one aspect of the present invention will be described below.

Figure 2:
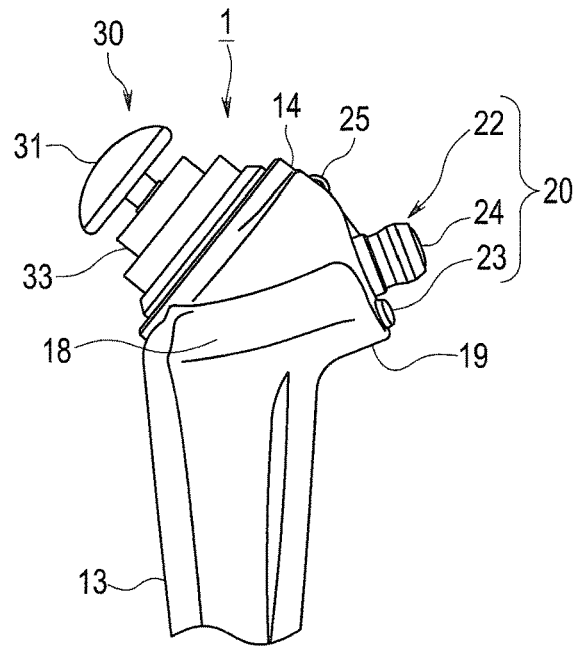
FIG. 2 is a right side view showing an appearance configuration of an operation portion of the endoscope according to one aspect of the present invention.
Figure 3:
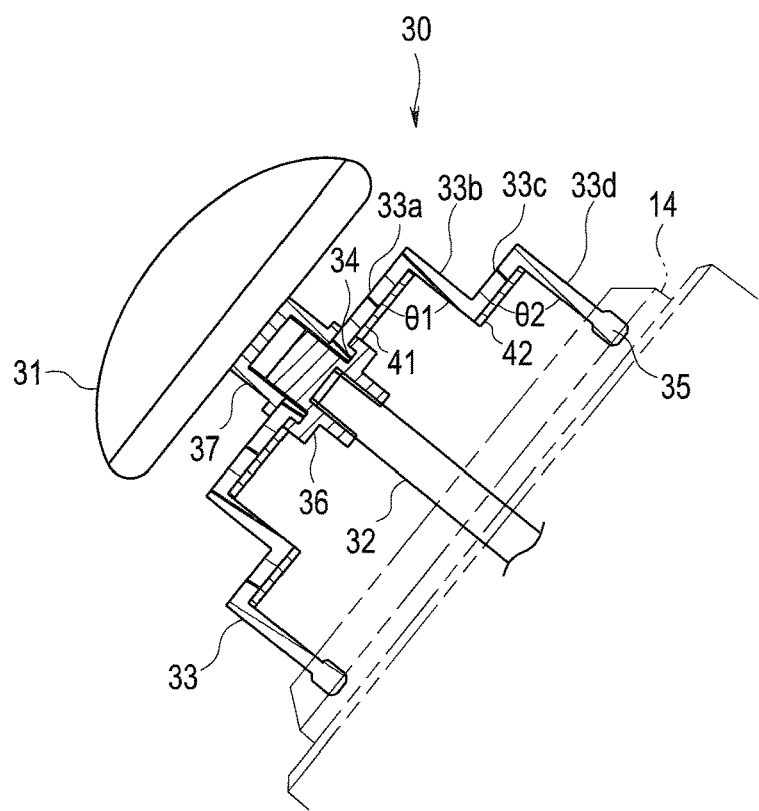
FIG. 3 is a partial sectional view showing a configuration of a bending operation lever portion according to one aspect of the present invention.
Figure 4:
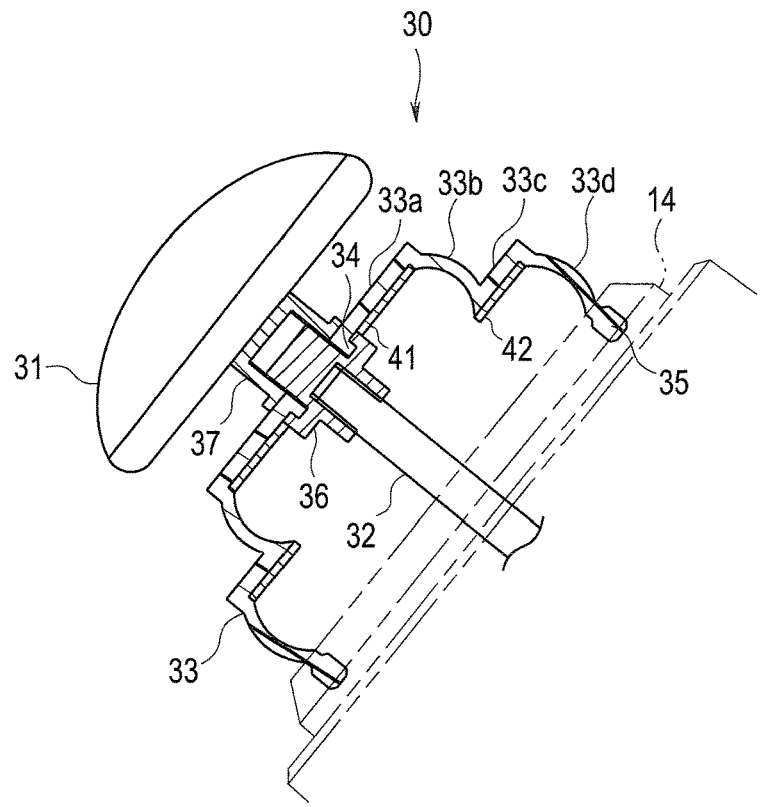
FIG. 4 is a partial sectional view showing a configuration of the bending operation lever portion in a state where positive pressure is applied during a leak test, according to one aspect of the present invention.

Note that FIG. 1 is a front view showing an appearance configuration of the endoscope, FIG. 2 is a right side view showing an appearance configuration of an operation portion of the endoscope, FIG. 3 is a partial sectional view showing a configuration of a bending operation lever portion, and FIG. 4 is a partial sectional view showing a configuration of the bending operation lever portion in a state where positive pressure is applied during a leak test.

The endoscope 1 of the present embodiment shown in FIGS. 1 and 2 is an electronic endoscopy. The endoscope 1 includes an insertion portion 2 formed in a shape of a slender tube, an operation portion 3 provided in a coupled manner to a proximal end of the insertion portion 2, a universal cord 4 being an endoscope cable extended from the operation portion 3, and an endoscope connector 5 provided at a distal end of the universal cord 4.

The insertion portion 2 of the endoscope 1 is made up of a tubular member that has flexibility and in which a distal end portion 6, a bending portion 7, and a flexible tube portion 8 are provided in a coupled manner in order from a distal end side.

Although not shown, an inside of the distal end portion 6 of the insertion portion 2 is provided with such elements as an objective optical system, an image pickup unit incorporating image sensors such as a CCD and a CMOS, and the like, an illumination optical system for performing irradiation with light transmitted by a light guide bundle, and a channel pipe for connecting and holding a treatment instrument channel.

The bending portion 7 of the insertion portion 2 is configured so as to be actively bendable in all circumferential directions around an insertion axis O, including vertical and horizontal (up-down/right-left) directions, in response to an operation input from a user or the like who is an operator of the operation portion 3.

The flexible tube portion 8 of the insertion portion 2 is made up of a tubular member having flexibility and being bendable passively. The flexible tube portion 8 has an image pickup cable, a light guide bundle, a treatment instrument insertion channel, and air/water feeding tubes inserted therein (none is shown).

The operation portion 3 of the endoscope 1 includes: a folded portion 11 connected to the flexible tube portion 8 in a state of covering a proximal end of the flexible tube portion 8; an insertion portion rotating dial 12 provided on a proximal end side of the folded portion 11 and capable of freely adjusting a rotational position of the insertion portion 2 around the insertion axis O; a grasping portion 13 provided in a coupled manner to a proximal end side of the insertion portion rotating dial 12 and graspable by a hand of the user or the like; and an operation portion body 14 provided in a coupled manner to a proximal end side of the grasping portion 13.

In the present embodiment, a circumferential direction of the insertion axis O as a longitudinal axis in the operation portion 3 or some other direction is defined by taking, as a reference, a state in which the user or the like grasps the grasping portion 13. More specifically, in the operation portion 3, longitudinal and horizontal directions (a front surface, a rear surface, and right and left side surfaces) are defined by taking the user or the like who grasps the grasping portion 13 as a reference.

The grasping portion 13 is formed in a horizontally symmetrical shape with respect to the insertion axis O and can be grasped with either a left hand or a right hand of the user or the like in the same manner.

A treatment instrument insertion portion 15 is provided on a distal-end-side front surface of the grasping portion 13. The treatment instrument insertion portion 15 includes a treatment instrument insertion opening 16, through which various treatment instruments, not shown, are inserted.

Inside the operation portion 3, the treatment instrument insertion opening 16 is communicated with the treatment instrument insertion channel through a division member (neither is shown). In the treatment instrument insertion portion 15, for example, a disposable forceps plug, which is not shown and is a cover member for blocking the treatment instrument insertion opening 16, is provided in a freely removable manner.

On the proximal end side of the grasping portion 13, the operation portion body 14 is configured of a hollow member formed in a substantially partially spherical shape, swollen mainly laterally and forward. On a front surface side of the operation portion body 14, operation buttons 20 are provided to execute a sucking function of the endoscope 1, various optical system functions, and the like.

The operation buttons 20 include, for example, a disposable suction valve 22 and two button switches 23 to which arbitrary functions such as a release button can be selectably allocated from various functions related to the endoscope 1, the suction valve 22 and the button switches 23 being mounted on the operation portion body 14 in a freely removable manner.

Note that the suction valve 22 includes a suction button 24 as an operation input member, and a tube connection portion 25 connected with a suction tube extended from an endoscope suction device being external equipment, not shown.

As shown in FIG. 2, on a rear surface side of the operation portion body 14, a bending operation lever portion 30 is provided as a bending operation means for performing a bending operation on the bending portion 7.

The universal cord 4 is extended from one side portion (e.g., a left side portion) of the operation portion body 14 through a cable folded portion 17.

Here, as shown in FIG. 1, a horizontal shape of the operation portion body 14 is a swollen shape horizontally symmetrical with respect to the insertion axis O. Each of right and left side surfaces on a distal end side of the operation portion body 14 is formed with a guiding recessed portion 18 for guiding a forefinger of the user or the like, grasping the grasping portion 13, to the operation buttons 20.

The universal cord 4 is a composite cable that has various signal lines that include the image pickup cable reaching the operation portion 3 from the distal end portion 6 side through an inside of the insertion portion 2 and further extending from the operation portion 3, the light guide bundle, and the air/water feeding tubes that allow flow of air/water feeding fluids (none is shown) inserted therein.

The endoscope connector 5 provided in an end portion of the universal cord 4 includes an electric connector portion 5a provided in a side surface portion and a light source connector portion 5b connected to a light source device being external equipment, not shown.

Note that a connector of an electric cable is connected to the electric connector portion 5a in a freely removable manner, the electric cable extending from a video processor that is external equipment, not shown. The light source connector portion 5b is provided with a light guide connector portion 5c in which a light guide bundle is accommodated.

Next, a configuration of the bending operation lever portion 30 provided in the operation portion body 14 will be described in more detail based on FIG. 3.

The bending operation lever portion 30 provided on the rear surface side of the operation portion body 14 is configured of, for example, a lever of a so-called joystick type that is tiltable to all directions including the vertical and horizontal directions.

As shown in FIG. 3, a tip portion of the bending operation lever portion 30 is provided with a finger contact portion 31, with which a thumb or some other finger of the user or the like can be brought into contact. Note that the bending operation lever portion 30 is provided such that the user or the like can operate the finger contact portion 31 with the thumb of the hand of the user or the like grasping the grasping portion 13.

In the bending operation lever portion 30, an operation shaft 32 being a lever shaft is connected to the finger contact portion 31, and an exterior cover 33 as a waterproof boot is provided for water-tightly sealing a periphery of the operation shaft 32 to form a sealed space inside the endoscope 1.

Inside the operation portion 3, a bending operation mechanism, not shown, is linked to the operation shaft 32 of the bending operation lever portion 30. The bending operation lever portion 30 can cause the bending portion 7 to perform a bending action in an arbitrary direction through a pulling operation of each pulling wire by the bending operation mechanism.

The exterior cover 33 of the bending operation lever portion 30 is configured of a resin material being an elastic member, such as flexible rubber, an inner periphery portion of which is close to the finger contact portion 31 and water-tightly covers an outside of the operation shaft 32, and an outer periphery portion of which is water-tightly fixed to the operation portion body 14 of the operation portion 3.

More specifically, the exterior cover 33 is configured of a cylindrical member forming a stair shape in cross section in which stairs are formed in a direction from an inner peripheral side close to the finger contact portion 31 to an outer peripheral side connected to the operation portion body 14.

In the exterior cover 33, respective sealings 34, 35, which form thick bead shapes in peripheral end portions on the inner peripheral side and the outer peripheral side, are formed integrally.

Of the sealings 34, 35, the sealing 34 on the inner peripheral side is pressurized by a water-tightness holder 36 to which the operation shaft 32 is fixed by screwing or the like, and a water-tightness cap 37 that is fixed to the water-tightness holder 36 by screwing or the like and provided so as to protrude from a center of a lower surface of the finger contact portion 31, so that the water-tightness is held between the finger contact portion 31 and the operation shaft 32.

On the other hand, of the sealings 34, 35, the sealing 35 on the outer peripheral side is pressurized and fixed by a cover holder including a plurality of holder rings, not shown, provided in the operation portion body 14, so that the water-tightness is held.

As thus described, the bending operation lever portion 30 that protrudes from the operation portion body 14 and is movable is provided in a state where the water-tightness is held from a position close to the finger contact portion 31 to the operation portion body 14.

The exterior cover 33 here has a two-step shape in cross section including: a first flat surface portion 33a, a first peripheral surface portion 33b, a second flat surface portion 33c, and a second peripheral surface portion 33d, the first flat surface portion 33a being one of first planes as a horizontal portion that is integrally formed with the sealing 34 on the inner peripheral side, the first peripheral surface portion 33b being one of second planes as a vertical portion, which is extended from the first flat surface portion 33a to the operation portion body 14 side, the second flat surface portion 33c being one of the first planes as a horizontal portion, extended in a radial direction from the first peripheral surface portion 33b, the second peripheral surface portion 33d being one of the second planes as a vertical portion that is extended from the second flat surface portion 33c to the operation portion body 14 side and integrally formed with the sealing 35 on the outer peripheral side.

Note that the exterior cover 33 is not restricted to the two-step shape in cross section but may have a shape of two or more steps in cross section.

Further, in the exterior cover 33, an angle θ1 formed by the first flat surface portion 33a and the first peripheral surface portion 33b having a predetermined angle is 90° here, and an angle θ2 formed by the second flat surface portion 33c and the second peripheral surface portion 33d having a predetermined angle is also 90° here. The angles θ1, θ2 formed by the respective flat surface portions 33a, 33c and peripheral surface portions 33b, 33d may only be 90° or larger (θ1, θ2≥90°).

On inner surface sides of the first flat surface portion 33a and the second flat surface portion 33c of the exterior cover 33, a first metal plate body 41 and a second metal plate body 42 that are each a rigid member formed of a metal such as stainless, aluminum, or brass, are molded integrally. Note that each of the first metal plate body 41 and the second metal plate body 42 is desirably formed of a material capable of bearing sterilization at high temperature and high pressure, but is not restricted to having metal properties, but may be a plate body using ceramic, glass, heat-resistant hard resin, or the like.

The first metal plate body 41 is a disk-shaped member that is provided on the inner surface side of the first flat surface portion 33a, and at the center of which a hole portion allowing insertion of the water-tightness holder 36 is formed. The second metal plate body 42 is a disk-shaped member that is provided on the inner surface side of the second flat surface portion 33c, and at the center of which a hole portion is formed.

That is, while the exterior cover 33 is formed of the resin material such as flexible rubber, the first flat surface portion 33a and the second flat surface portion 33c that are substantially orthogonal to the operation shaft 32 are rigid regions as hardly deformable regions that are not deformed due to provision of the first metal plate body 41 and the second metal plate body 42, and the first peripheral surface portion 33b and the second peripheral surface portion 33d that are substantially parallel to the operation shaft 32 are flexible regions as easily deformable regions, so as not to impair operability of the bending operation lever portion 30.

In the endoscope 1 of the present embodiment as thus configured, during a leak test for determining whether or not the internal water-tightness has been ensured at the time of after-use cleaning, when positive pressure is applied to the inside of the endoscope 1 for pressurization to cause an increase in internal pressure, as shown in FIG. 4, the first flat surface portion 33a and the second flat surface portion 33c are not deformed and only the first peripheral surface portion 33b and the second peripheral surface portion 33d are easily swollen in the radial direction.

That is, even when the internal pressure increases during the leak test, folding of the exterior cover 33 is prevented because the first flat surface portion 33a and the second flat surface portion 33c are not deformed.

Further, in the exterior cover 33, the angle θ1 formed by the first flat surface portion 33a and the first peripheral surface portion 33b is 90° or larger, and the angle θ2 formed by the second flat surface portion 33c and the second peripheral surface portion 33d is also 90° or larger, so that the first flat surface portion 33a and the second flat surface portion 33c hardly come into contact with each other even when the first peripheral surface portion 33b and the second peripheral surface portion 33d are swollen in the radial direction.

With such a configuration formed, even when the endoscope 1 is automatically cleaned with the endoscope cleaner that performs the leak test during a cleaning process, a folded portion is not generated in the exterior cover 33, thus eliminating the need to clean the endoscope 1 again manually and enabling prevention of complicated labor.

Therefore, even when the endoscope 1 of the present embodiment is used for an endoscope cleaner that implements a series of processes from the leak test to the cleaning, the endoscope 1 can be configured to prevent folding of the exterior cover 33 that covers an outer side portion of the bending operation lever portion 30 in a state where positive pressure is applied to the inside during the leak test process, thus saving labor for cleaning.

Note that the endoscope 1 is not restricted to being cleaned with the endoscope cleaner that implements a series of processes from the leak test to the cleaning, but may naturally be cleaned manually or may be cleaned using an endoscope cleaner that does not perform the leak test during the cleaning process.

First Modification

Figure 5:
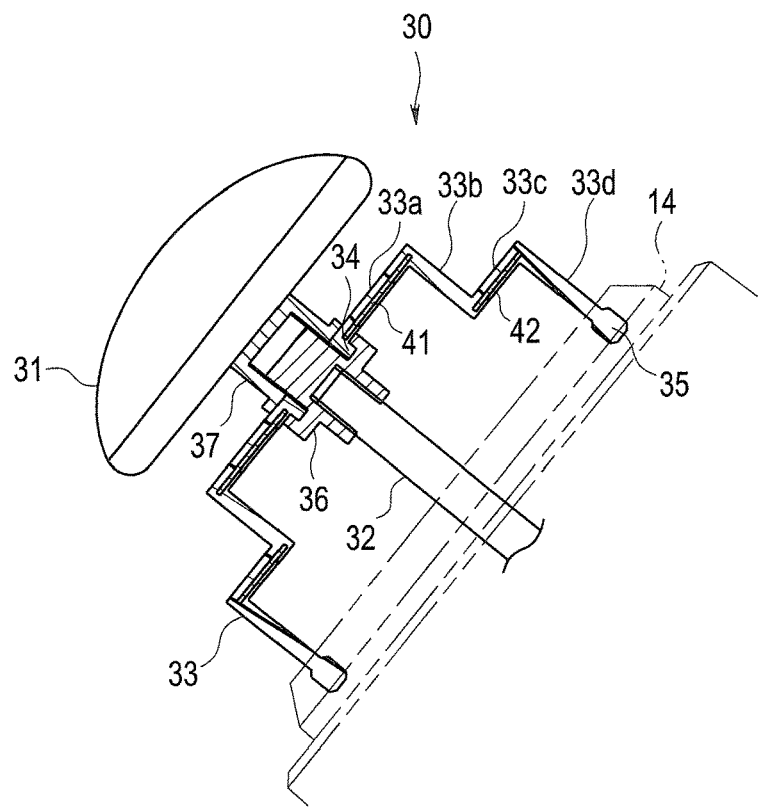
FIG. 5 is a partial sectional view showing a configuration of a bending operation lever portion in a first modification according to one aspect of the present invention.

FIG. 5 is a partial sectional view showing a configuration of a bending operation lever portion in a first modification.

As shown in FIG. 5, in the exterior cover 33, the first metal plate body 41 and the second metal plate body 42 may be buried inside the first flat surface portion 33a and the second flat surface portion 33c.

Second Modification

Figure 6:
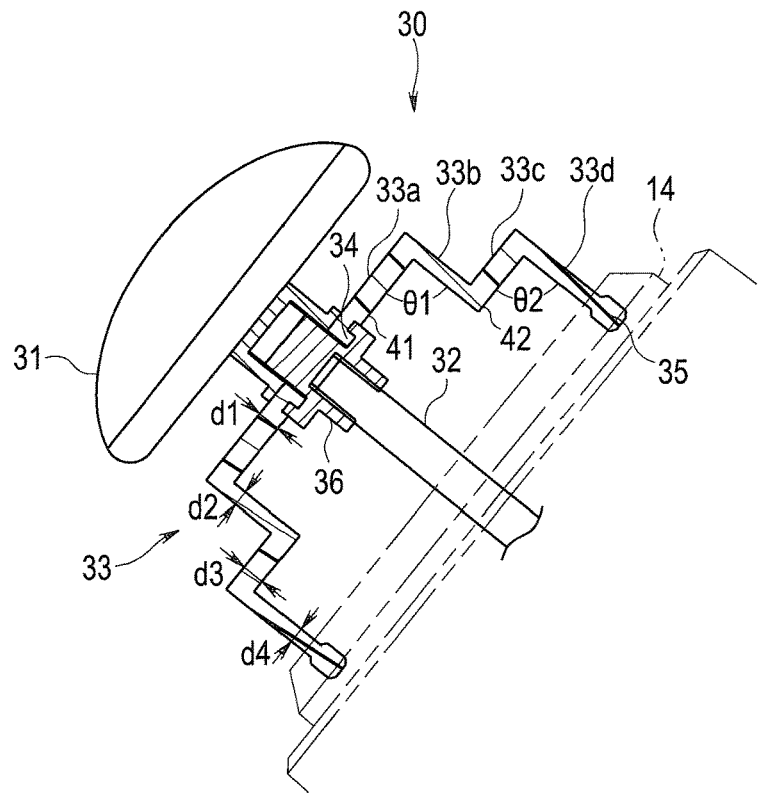
FIG. 6 is a partial sectional view showing a configuration of a bending operation lever portion in a second modification according to one aspect of the present invention.
Figure 7:
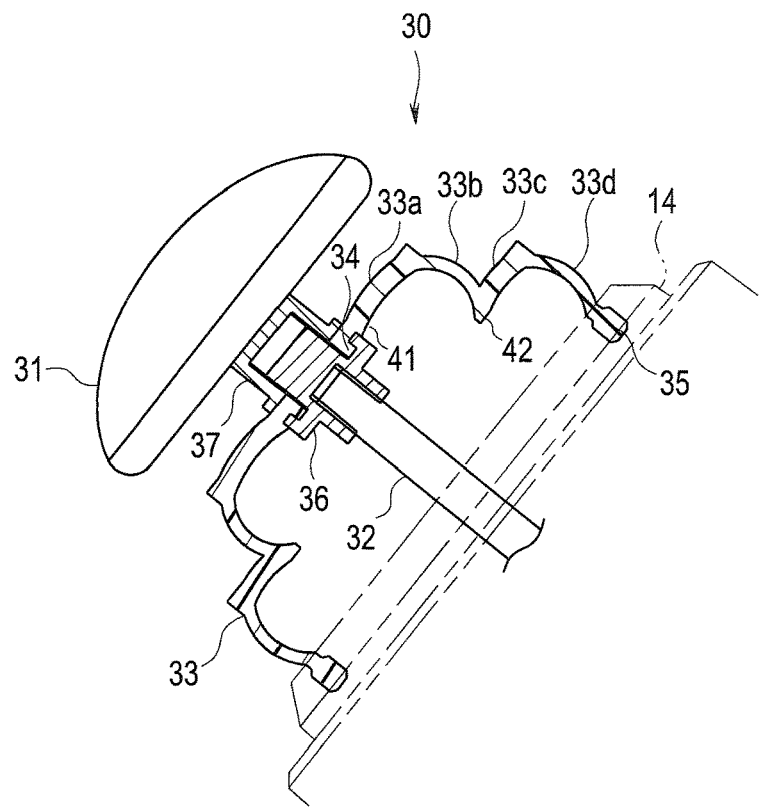
FIG. 7 is a partial sectional view showing a configuration of the bending operation lever portion in a state where positive pressure is applied during a leak test in the second modification according to one aspect of the present invention.

FIG. 6 is a partial sectional view showing a configuration of a bending operation lever portion in a second modification, and FIG. 7 is a partial sectional view showing a configuration of the bending operation lever portion in a state where positive pressure is applied during the leak test.

As shown in FIG. 6, in the exterior cover 33 of the present modification, thicknesses of the first flat surface portion 33a and the second flat surface portion 33c are larger than thicknesses of the first peripheral surface portion 33b and the second peripheral surface portion 33d.

More specifically, in the exterior cover 33, in order not to impair the operability of the bending operation lever portion 30, a thickness d2 of the first peripheral surface portion 33b and a thickness d4 of the second peripheral surface portion 33d are set to be approximately 0.5 mm to 1.0 mm and a thickness d1 of the first flat surface portion 33a and a thickness d3 of the second flat surface portion 33c are set to be approximately 1.5 to three times as large as the thicknesses d2, d4.

That is, while the exterior cover 33 is formed of the resin material such as flexible rubber, the first flat surface portion 33a and the second flat surface portion 33c are hardly deformable regions set to be hardly deformed due to large thicknesses, and the first peripheral surface portion 33b and the second peripheral surface portion 33d are easily deformable regions set to be flexible, so as not to impair the operability of the bending operation lever portion 30.

In the endoscope 1 of the present modification, during the leak test for determining whether or not the internal watertightness has also been ensured at the time of after-use cleaning, when positive pressure is applied to the inside of the endoscope 1 for pressurization to cause an increase in internal pressure, as shown in FIG. 7, the first flat surface portion 33a and the second flat surface portion 33c are deformed in a small amount, whereas the first peripheral surface portion 33b and the second peripheral surface portion 33d are deformed in a large amount and are easily swollen in the radial direction.

Therefore, in the present modification, even when the internal pressure increases during the leak test, folding of the exterior cover 33 is also prevented because the first flat surface portion 33a and the second flat surface portion 33c are hardly deformed.

During the leak test, the inside of the endoscope 1 is pressurized to about 30 kpa, followed by measurement, and hence it is preferable to set the first flat surface portion 33a and the second flat surface portion 33c of the exterior cover 33 to have the thicknesses of d1, d2 that remain unchanged even when the pressure of 30 kpa is applied.

With such a configuration formed, the endoscope 1 includes the first metal plate body 41 or the second metal plate body 42 being not superfluously configured, in addition to having the function effect described in the above embodiment, so that it is also possible to improve assemblability and weight saving.

Although the configuration where the exterior cover 33 is formed of the elastic member such as rubber has been illustrated in the embodiment and the modifications described above, at least the first peripheral surface portion 33b and the second peripheral surface portion 33d may only be formed of the elastic member.

Note that the invention described in the above embodiment is not restricted to the embodiment and the modifications, but various modifications can be made in a scope not deviating from the gist of the invention in an implementation phase. Further, the above embodiment includes various stages of inventions, and appropriate combination of a plurality of disclosed constituent features enables extraction of various inventions.

For example, when the described problem can be solved and the described effect can be obtained even if some constituent features are deleted from all the constituent features shown in the embodiment, the configuration from which some constituent features have been deleted can be extracted as an invention.

According to the present invention, it is possible to provide the endoscope and the exterior cover for the endoscope, which, even when used for an endoscope cleaner that implements a series of processes from a leak test to cleaning, can prevent folding of the exterior cover that covers the outer side portion of the operation lever portion in a state where positive pressure is applied to the inside during a leak test process, so as to save a manual leak test and make any type of automatic endoscope cleaner selectable.

What is claimed is:
1. An endoscope comprising:
an operation portion provided on a proximal end side of an insertion portion, the insertion portion including a bending portion;

an operation lever provided in the operation portion, the operation lever includes an operation shaft, and the operation lever being configured to adjust a bending angle of the bending portion in conjunction with a tilting operation of the operation lever; and an exterior cover water-tightly fixed to the operation portion so as to cover an outer periphery of the operation shaft, the exterior cover including first, second and third deformation portions, the third deformation portion being formed at a predetermined angle with respect to each of the first and second deformation portions, the first and second deformation portions being provided at first and second locations, respectively, and the third deformation portion being provided between the first and second locations, the first and second deformation portions being substantially planar and extending radially outward from a longitudinal axis direction of the operation lever, the third deformation portion connecting a radially outer end of the first deformation portion to a radially inner end of the second deformation portion, wherein, the first, second and third deformation portions are configured such that when a pressure of 30 kPa or more is applied to an inside of the exterior cover, a deformation amount of the third deformation portion is larger than a deformation amount of each of the first and second deformation portions.

2. The endoscope according to claim 1, wherein the third deformation portion is formed of a peripheral surface substantially parallel to the longitudinal axis of operation shaft.

3. The endoscope according to claim 1, wherein at least the third deformation portion is formed of an elastic member.

4. The endoscope according to claim 1, wherein the first and second deformation portions comprise a rigid member.

5. The endoscope according to claim 4, wherein the rigid member comprises a metal plate body molded integrally on an inner surface side of the first and second deformation portions.

6. The endoscope according to claim 4, wherein the rigid member comprises a metal plate body embedded inside the first and second deformation portions.

7. The endoscope according to claim 1, wherein a thickness of the first and second deformation portions is formed to be larger than a thickness of the third deformation portion.

8. The endoscope according to claim 7, wherein the thickness of the first and second deformation portions is 1.5 to 3 times as large as the thickness of the third deformation portion.

9. The endoscope according to claim 8, wherein the thickness of the third deformation portion is 0.5 mm to 1.0 mm.

10. The endoscope according to claim 1, wherein the exterior cover having first and second fixed ends and the deformable portion being formed between the first and second fixed ends, the deformable portion including the first, second and third deformation portions.

11. The endoscope according to claim 1, wherein the third deformation portion directly connects the radially outer end of the first deformation portion to the radially inner end of the second deformation portion.

12. An exterior cover for an endoscope, which is provided in an operation portion of the endoscope, and water-tightly fixed to the operation portion so as to cover an outer periphery of an operation shaft configured to perform a tilting operation, and in which first, second and third deformation portions are provided, the third deformation portion having a predetermined angle with respect to each of the first and second deformation portions, the first and second deformation portions being provided at first and second locations, respectively, the third deformation portion being provided between the first and second locations, the first and second deformation portions being substantially planar and extending radially outward from a longitudinal axis direction of the operation lever, the third deformation portion connecting a radially outer end of the first deformation portion to a radially inner end of the second deformation portion, wherein, the first, second and third deformation portions are configured such that when a pressure of 30 kPa or more is applied to an inside of the exterior cover, a deformation amount of the third deformation portion is larger than a deformation amount of each of the first and second deformation portions.

13. An endoscope comprising the exterior cover for the endoscope according to claim 12.

14. The exterior cover for an endoscope according to claim 12, wherein the first and second deformation portions comprise a rigid member and the rigid member comprises a metal plate body molded integrally on an inner surface side of the first and second deformation portions.

15. The exterior cover for an endoscope according to claim 12, wherein the first and second deformation portions comprise a rigid member and the rigid member comprises a metal plate body embedded inside the first and second deformation portions.

16. The exterior cover for an endoscope according to claim 12, wherein the exterior cover having first and second fixed ends and the deformable portion being formed between the first and second fixed ends, the deformable portion including the first, second and third deformation portions.

17. The exterior cover for the endoscope according to claim 12, wherein the thickness of the first and second deformation portions is 1.5 to 3 times as large as the thickness of the third deformation portion.

18. The exterior cover for the endoscope according to claim 17, wherein the thickness of the third deformation portion is 0.5 mm to 1.0 mm.

19. The exterior cover for the endoscope according to claim 12, wherein the third deformation portion directly connects the radially outer end of the first deformation portion to the radially inner end of the second deformation portion.

* * * * *